US006420106B1

(12) United States Patent
Gyllensten et al.

(10) Patent No.: US 6,420,106 B1
(45) Date of Patent: Jul. 16, 2002

(54) METHOD AND KIT FOR EARLY CANCER PREDICTION

(75) Inventors: Ulf Gyllensten; Agnetha Josefsson; Patrik Magnusson, all of Uppsala (SE)

(73) Assignee: Quantovir AB, Uppsala (SE)

( * ) Notice: Subject to any disclaimer, the term of this patent is extended or adjusted under 35 U.S.C. 154(b) by 0 days.

(21) Appl. No.: 09/588,356

(22) Filed: Jun. 7, 2000

Related U.S. Application Data (60) Provisional application No. 60/138,286, filed on Jun. 9, 1999.

(51) Int. Cl.$^7$ ............................... C12Q 1/70; C12P 1/68; C07H 21/02; C07H 21/04
(52) U.S. Cl. ............................... 435/5; 435/6; 536/23.1; 536/24.3
(58) Field of Search ............................... 435/5, 6, 91.2; 536/23.1, 24.3; 935/76, 77, 78

(56) References Cited

U.S. PATENT DOCUMENTS

| | | | |
|---|---|---|---|
| 5,283,171 A | | 2/1994 | Manos et al. |
| 5,346,811 A | * | 9/1994 | Galindo-Castro et al. |
| 5,364,758 A | * | 11/1994 | Meijer et al. |
| 5,484,699 A | * | 1/1996 | Bouma et al. |

FOREIGN PATENT DOCUMENTS

| | | |
|---|---|---|
| EP | 0301968 A1 | 2/1989 |
| WO | WO9108312 | 6/1991 |

OTHER PUBLICATIONS

Ho et al., J. of the National Cancer Institute 87 (18) : 1365–1371 (1995).*
Josefsson et al., Lancet 355 :2189–2193 (2000).*
Hammond et al., Virology 254 (1) : 37–49 (Feb.1999)—Abstract Only.*
Munoz et al., IARC Scientific Publications (1992) (119) 251–61.*
Martina Samiotaki et al., "Seven–Color Time–Resolved Fluorescence Hybridization Analysis of Human Papilloma Virus Types," Analytical Biochemistry, vol. 253, 1997, pp. 156–161.
Nathalie Ylitalo et al., "Detection of Genital Human Papillomavirus by Single–Tube Nested PCR and Type–Specific Oligonucleotide Hybridization," Journal of Clinical Microbiology, vol. 33, No. 7, Jul. 1995, pp. 1822–1828.
Ho Gy et al., "Persistent genital human papillomavirus infection as a risk factor for persistent cervical dysplasia," Journal of the National Cancer Institute, Sep. 20, 1995, 87 (18) pp. 1365–1371 (Medline Accession No. 95387422).
H. Ikenberg et al., "Semiquantitative analysis of human papillomavirus DNA in cervical intraepithelial neoplasia by a differential polymerase chain reaction," Journal of Obstetrics and Gynaecology, 17/2 (176–179), 1997 (Dialog Accession No. 00599850).
Y. Taoufik et al., "Prognostic value of JC virus load in cerebrospinal fluid of patients with progressive multifocal leukoencephalopathy," Journal of infectious diseases, Dec. 1998, 178 (6), pp. 1816–1820 (Medline Accession No. 99034675).

* cited by examiner

*Primary Examiner*—Ethan C. Whisenant
(74) *Attorney, Agent, or Firm*—Young & Thompson

(57) ABSTRACT

The present invention is within the field of early cancer prediction. More closely, the invention relates to a method and kit for predicting virus-associated cervical cancer in a human subject. In the method the amount of viral nucleic acid is normalized in relation to the amount of sample from a human subject. Using specific primers and probes in a DNA amplification kit of the invention, a value of relative viral load is obtained which enables prediction of risk of cervical cancer several years before any symptoms thereof.

14 Claims, 3 Drawing Sheets

METHOD AND KIT FOR EARLY CANCER PREDICTION

This application claims the benefit of U.S. Provisional Application No. 60/138,286 filed Jun. 9, 1999.

FIELD OF THE INVENTION

The present invention is within the field of early cancer prediction. More closely, the invention relates to a method and kit for predicting virus-associated cervical cancer in a human subject.

BACKGROUND OF THE INVENTION

Infection by certain subtypes of human papillomavirus (HPV), in particular HPV 16 and HPV 18, has long been recognized as a major risk factor for cervical cancer and about 95% of cancer biopsies contain HPV DNA. While infection with HPV is common in young women in the ages 16–24, only less than 1% of women with oncogenic HPV smears develop cervical cancer. Therefore, known methods for testing for presence of HPV has a low predictive value.

Within prior art there are two main strategies to predict or diagnose cervical cancer. One strategy uses squamous intraepithelial lesion in cytology, or cervical dysplasia, as an indication of progression to cervical cancer. The other main strategy is to detect HPV nucleic acid in a patient sample either directly or following amplification of said nucleic acid, wherein the presence of HPV nucleic acid is taken as an indication of possible progression to cervical cancer.

Prior art has also concentrated on determining the exact HPV types, for example, U.S. Pat No. 5,580,970 describes amplification of low-oncogenic HPV genes, such as HPV 6 and 11, as an indication of lower risk of progression to serious cervical cancer, and high-oncogenic HPV genes as an indication of higher risk.

U.S. Pat. No. 5,795,722 describes amplification of (i) one or more control nucleic acids together with amplification of (ii) a conserved region of an analyte nucleic acid from a suspected pathogen in a patient sample as well as (iii) a region of the analyte nucleic acid used for sequencing. Following amplification, the sequencing region is captured from the amplification mixture and the remaining fragment mixture is separated electrophoretically to determine the relative amounts of conserved fragments and control fragments. Thereafter, the sequence of the sequencing region is determined as well as its pathogenic source.

Ylitalo et al. in J. Clin. Microbiol. 33: 1822–1828 describes detection of genital HPV types by amplification of the conserved E1 region of oncogenic HPV types. Quantification of viral load is not discussed.

Hitherto there is no known method of predicting cervical cancer several years before development of cancer.

SUMMARY OF THE INVENTION

The present invention provides a method and kit enabling early prediction of the clinical outcome of cervical cancer in situ (CCIS). According to the present invention, cervical cancer can be predicted in HPV positive women where the initial HPV positive smears were sampled several years before development of cancer.

In a first aspect, the present invention provides a method to predict the risk of progression to virus-associated cancer in a human subject, comprising a) measuring the amount of a viral nucleic acid sequence or fragment thereof in a sample from the human subject;

b) measuring the amount of said sample;

c) relating the value from a) to the value from b) to obtain a value of relative viral load in said sample. In one embodiment the amount of said sample is measured by measuring a human nucleic acid sequence or fragment thereof, d) using said value to estimate risk of progression to cervical cancer, with higher viral load meaning an increased risk of progression to cervical cancer.

The viral nucleic acid sequence is preferably nucleic acid from cervical cancer-associated genital human papillomavirus (HPV)-types, such as HPV 16, 18, 31, 33, 35, 39, 45, 51, 52, 56, and 58. In a preferred embodiment, the viral nucleic acid is derived from the E1 gene, the E6 gene, the E7 gene, the L1 gene, or fragment(s) thereof. The human nucleic acid sequence is preferably genomic DNA from a nuclear gene.

In the method according to the invention, the measuring in step a) and b) is made by known methods for quantitative DNA or RNA analysis, such as polymerase chain reaction (PCR), in situ hybridization, NASBA, 3SR, hybrid capture etc.. Alternatively, the amount of the biological sample is measured by counting cells, cell staining, cell fluorescence, total DNA amount, using a technical device for obtaining identical amounts of biological sample, or using volume, weight or other means of normalizing for sample amount.

In a second aspect, the invention provides a kit for predicting HPV-associated cervical cancer by amplification of viral nucleic acid, comprising a) primers specific for a region of the conserved E1 gene of oncogenic HPV types; and b) primers specific for genomic nucleic acid in a sample from a human subject.

The primers in b) may be selected from any nuclear gene, preferably a single copy gene. The kit may also comprise DNA intercalating compounds, such as ethidium bromide and SYBR® Green.

In a preferred embodiment, the kit also comprises labelled HPV specific probes; and labelled probes specific for human genomic DNA. The labels may be fluorophores, radioactive isotopes, compounds for chemiluminiscent detection etc.. Examples of fluorophores are FAM (6-carboxyfluorescein), HEX (hexachloro-6-carboxyfluorescein), TET (tetrachloro-6-carboxyfluorescein), JOE (2,7-dimethoxy-4,5-dichloro-6-carboxyfluorescein), TAMRA (6-carboxytetramethylrhodamine), ROX (6-carboxy-X-rhodamine), Cy5 (cyanine).

Preferred HPV probes are:

HPV 16 probe: 5'-ATAATCTCCTTTTTGCAGCTCTACTTTGTTTTT-3'
HPV 18 probe: 5'-CCGCCTTTTTGCCTTTTTCTGCCCACTAATT-3'
HPV 31 probe: 5'-TCTTCGTTTTGCTGTTTTACTGTTATTTTCTAT-3'
HPV 33 probe: 5'-TTTTCGTTTTCTGTATGTGCATTCTTTATTTTT-3'
HPV 35 probe: 5'-TCGTCGCTTTCGTGCTGTATTTTTATTTTCA-3'

DETAILED DESCRIPTION OF THE INVENTION

The present invention will now be described more closely below in association with the accompanying drawings, in which.

The present inventors have studied the relative viral load of HPV as a determinant of progression to cervical cancer in situ (CCIS). The relative viral load was analyzed in archival smears by a quantitative DNA amplification method. Multiple samples were obtained from each woman over a period of 26 years. A total of 2081 smears were obtained from 478 cases and 1754 smears from 608 controls.

The DNA of the smears was isolated and assayed for the amount of HPV 16 using an amplification of a fragment of 180 bp of the E1 open reading frame and a dual-labeled type-specific probe. The invention will be exemplified with a HPV 16 specific probe. However, the method of the invention is not limited to this one but it is expected that all of the above mentioned probes as well as probes similarly designed for other oncogenic types will provide satisfactorily results.

EXPERIMENTAL SECTION

DNA Extraction From Archival Smears

DNA extraction from archival Papanicolau stained smears was performed by the following procedure: a xylen incubation, a destaining by 95% ethanol, a proteinase K treatment (60° C. minimum 1 h) and subsequently a protein precipitation by saturated ammonium acetate. The DNA supernatant was recovered with ethanol, the pellet washed with 70% ethanol, dried and dissolved in 200 µl TE-low (10 mM Tris-HCL, pH 7.4, 0.1 mM EDTA).

PCR Amplification

The PCR amplification was performed in a 50 µl volume including 50 mM KCl, 10 mM tris-HCl (pH 8.4), 10 mM EDTA, 60 nM passive reference dye (Rox), 5 mM MgCl$_2$, 0.25 µM HPV E1 5' primer(s), 0.5 µM HPV E1 3' primer(s), HPV-specific dual-labeled probe at a concentration of 100 nM, dATP, dCTP and dGTP each at a concentration of 200 µM, 400 µM dUTP, 0.5 U of uracil N'-glycosylase (AmpErase UNG; Perkin-Elmer), 1.25 U of DNA polymerase (Amplitaq Gold; Perkin-Elmer), and 2–10 µl of DNA from the smear. The amount of DNA added to the PCR mixture represents 1 to 5% of the DNA obtained from a cervical smear. To reduce the complexity of the primers we constructed a 5' primer mix consisting of only two primers (HPVE116L 5'-TACAGGTTCTAAAACGAAAGT-3' specific for HPV 16 and 5'-HPVE118L TGCATGTTTTAAAACGAAAGT-3' specific for HPV 18), and a 3' primer mix consisting of three primers (HPVE116R 5'-TTCCACTTCAGTATTGCCATA-3' specific for HPV 16, HPVE118R 5'-TTCCACTTCAGAACAGCCATA-3' specific for HPV 18 and HPVE1RE 5'-TRYRKGMNYTAAAACGAAAGT-3' specific for HPV 30–60, wherein R=A or G, Y=C or T, K=G or T, M=A or C, S=G or C, W=A or T, N=A, T, C or G, B=C, G, or T, D=A, G, or T, H=A, C, or T, V=A, C or G.) It is also possible to use the HPV 16 specific or HPV 18 specific 5' and 3' primers alone or in combination with each other.

The fluorescent probes were 30–33 bp in length to ensure a higher Tm than for the primers. The following HPV 16 probe: FAM-5'ATAATCTCCTTTTTGCAGCTCTACTTTGTTTTT-3'TAMRA was used in an amplification and detection assay, using an ABI Prism 7700, Sequence detection system (Perkin Elmer Inc.). The amplification ramp included two hold programs (1) 2 min. at 50° C. to activate the decontamination enzyme, Uracile N' glycosylase (UNG) followed by (2) 10 min. at 95° C. to inactivate the UNG and release the activity of the DNA polymerase. This was followed by a two-step cycle consisting of a melting step for 15 sec. at 95° C. and annealing for 1 min. at 55° C., for a total of 50 cycles. To monitor contamination, approximate 8 tubes with only PCR components without DNA template were included. The threshold cycle was calculated using the Sequence Detection System software and the baseline was set automatically (10 SD above background in the first 3–15 cycles). Since all calculations were made on the Ct values directly, no standard curves were used.

Normalization of HPV DNA and Genomic DNA

Smear samples varied substantially in the threshold cycle number (Ct), representing the amplification cycle number at which the detection signal significantly exceed the baseline, potentially reflecting a difference in HPV DNA copy number of at least 100-fold between individual smears (data not shown). Due to the nature of the procedure used for sampling of cervical epithelial cells, HPV copy number differences may reflect the number of cells sampled. To normalize the HPV estimates for the amount of genomic DNA present in individual samples, a nuclear gene, β-actin, was quantitated in all smears, using the same amplification method. The nuclear DNA may be any nuclear DNA, preferably a single copy gene. The invention is not dependent on the way HPV DNA is normalized to nuclear DNA. The amount of viral DNA should be related to genomic nuclear DNA in any suitable way to provide a value of the relative viral load. For example, the relation can be the amount of viral DNA divided by the amount of genomic nuclear DNA.

Figure 1:
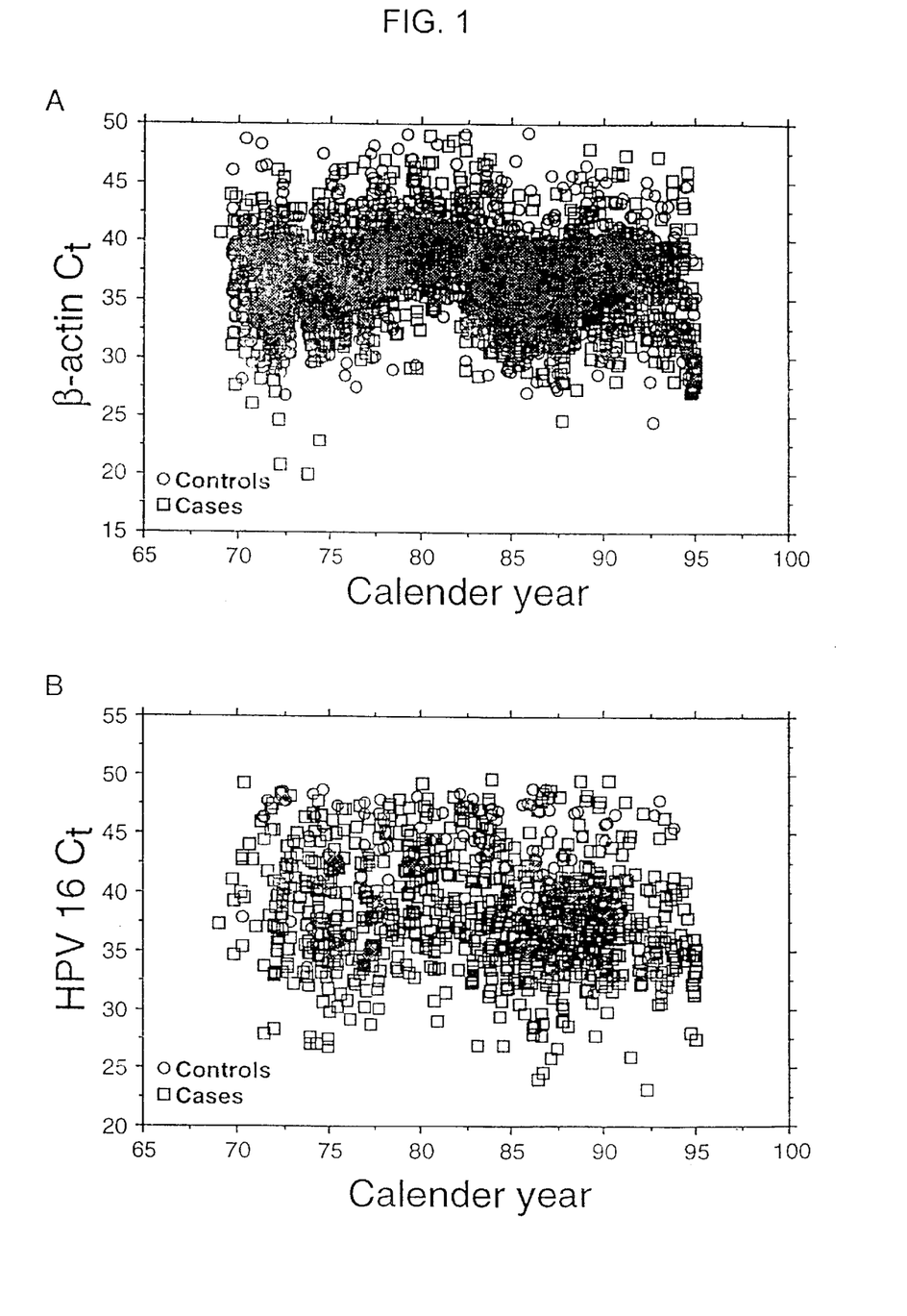
FIG. 1A shows distribution of β-actin threshold cycle (Ct) values for case (open squares) and control (open circles) smears, by calendar year of preparation of the smears (1969–1995).
FIG. 1B shows distribution of HPV 16 threshold cycle (Ct) values for case (open squares) and control (open circles) smears, by calendar year of preparation of the smears (1969–1995).

As mentioned above, the smears analyzed were prepared over a period of almost 26 years, and the procedure and reagents used for the preparation of smears may have changed over this time, potentially influencing the results. The median distribution of β-actin among cases (Ct=37.30) and (Ct=37.58) for the controls did not differ which indicates that there is no difference in DNA quality between the groups (see Table 1 below). The distribution of threshold (Ct) values for β-actin did not show any significant trend over time and was not significantly different between case and control smears (FIG. 1).

Results

Figure 2:
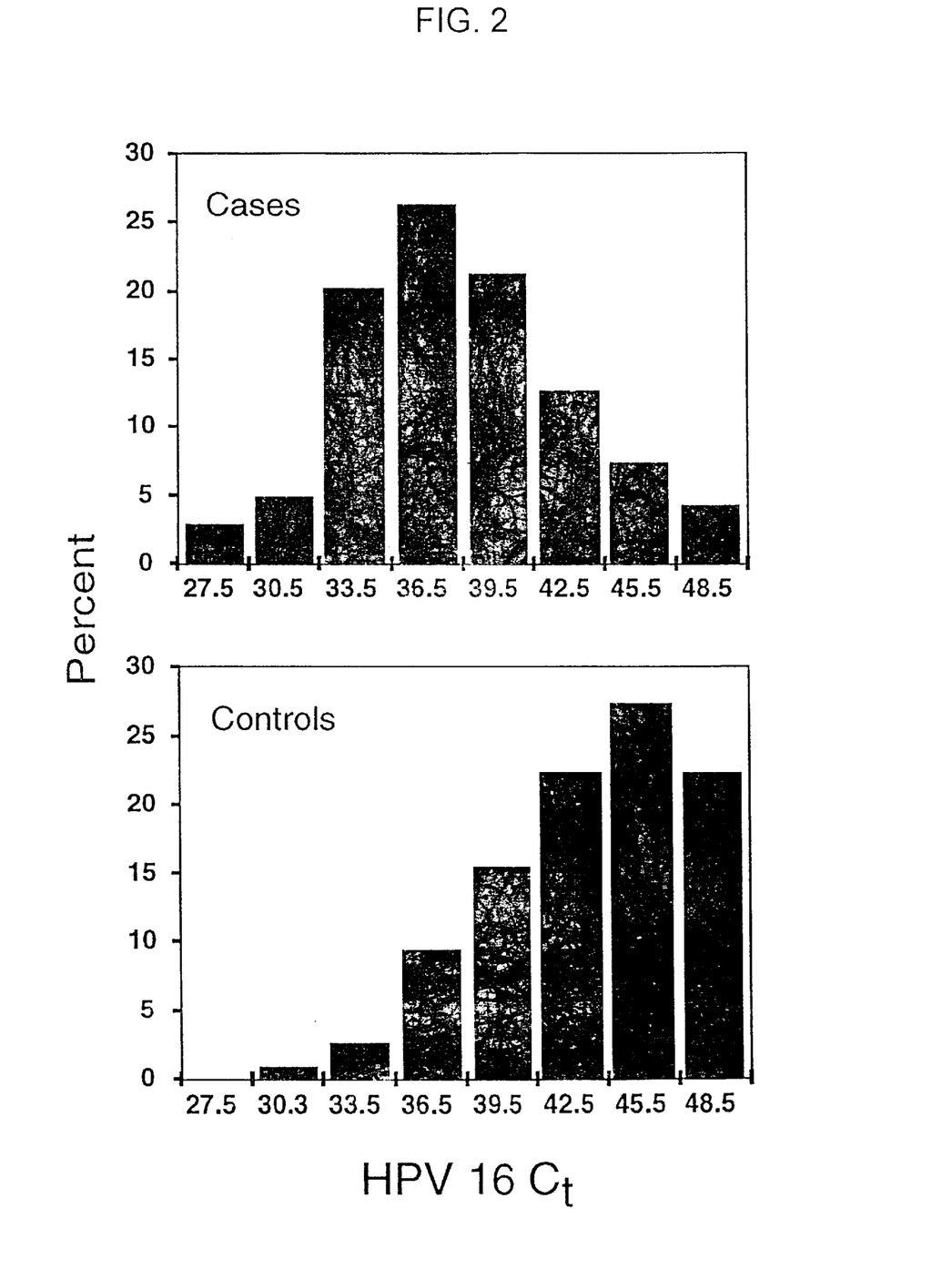
FIG. 2 shows distribution of HPV 16 threshold cycle (Ct) values for control (upper histogram) and case (lower histogram) smears. The HPV 16 Ct values (on the X-axis) were divided into eight groups, the mid group value of each is shown. Absolute frequency of smears on Y-axis.

A total of 871 smears from cases and 117 smears from controls were typing positive for HPV 16 (Table 1). The distribution of Ct values differs considerably between the cases and controls (FIG. 2), with a median of Ct=37.59 in cases and Ct=43.88 in controls (Table 1).

TABLE 1

Characteristics of the participants.

|  | Cases | Controls |
|---|---|---|
| No of women | 478 | 608 |
| β-actin positive smears |  |  |
| total number | 2081 | 1754 |
| median (range) | 4 (1–17) | 2 (1–14) |
| 75% percentile | 6 | 4 |
| Distribution of β-actin $C_t$ |  |  |
| min | 19.96 | 24.61 |
| 25% percentile | 35.04 | 35.44 |
| median | 37.30 | 37.58 |
| 75% percentile | 39.10 | 39.24 |
| max | 49.08 | 49.30 |

TABLE 2

Results of conditional logistic regression analysis of cases and controls among β-actin positive women.

| Categories* | $C_t$-HPV mean | | $C_t$-HPV max | | $C_t$-HPV min | |
|---|---|---|---|---|---|---|
|  | No of cases/controls | OR (95% CI)† | No of cases/controls | OR (95% CI)† | No of cases/controls | OR (95% CI)† |
| HPV − | 212/464 | 1 | 212/464 | 1 | 212/462 | 1 |
| HPV +, $C_t$ [44.8;50] | 27/32 | 2.00 (1.07–3.76) | 45/37 | 2.75 (1.59–4.74) | 25/31 | 1.86 (0.98–3.54) |
| HPV +, $C_t$ [41.25;44.8] | 41/18 | 4.36 (2.28–8.34) | 62/13 | 8.90 (4.45–17.80) | 33/16 | 3.75 (1.89–7.44) |
| HPV +, $C_t$ [38.99;41.25] | 48/12 | 8.08 (3.78–17.25) | 47/13 | 8.52 (4.14–17.55) | 22/12 | 3.60 (1.58–8.15) |
| HPV +, $C_t$ [36.66;38.99] | 52/7 | 18.75 (7.09–49.54) | 35/6 | 15.53 (5.55–43.43) | 40/9 | 11.06 (4.51–27.13) |
| HPV +, $C_t$ < 36.66 | 58/2 | 68.83 (15.81–299.64) | 37/2 | 42.86 (9.54–192.58) | 106/3 | 55.87 (17.23–181.19) |

*Categories are calculated on each 20 percentile of the distribution of the mean $C_t$ HPV 16 value for each woman.
†Adjusted for β-actin.

TABLE 1-continued

Characteristics of the participants.

|  | Cases | Controls |
|---|---|---|
| HPV 16 positive smears |  |  |
| total number | 871 | 117 |
| no of women with no positive smear | 190 | 509 |
| no of women with one or more positive smear | 288 | 99 |
| Distribution of HPV 16 $C_t$ |  |  |
| min | 23.13 | 31.49 |
| 25% percentile | 34.74 | 40.08 |
| median | 37.59 | 43.88 |
| 75% percentile | 40.92 | 46.77 |
| max | 49.72 | 49.90 |

Since there is an inverse relationship between $C_t$ and viral copy number, the difference between cases and controls is consistent with a higher average viral load in the cases. The $C_t$ values for HPV 16 does not show any trend over calendar time, and the difference between patients and controls appears constant over calendar time (FIG. 1B). Thus, the differences in HPV 16 $C_t$ values between patients and controls cannot be explained by variation in DNA quality over calendar time.

The relationship between viral load (HPV 16 $C_t$) and risk of disease was examined using conditional logistic regression analysis. The odds ratio (OR), based on the mean of all smear samples from a woman, are statistically significant for each 20 percentile, and show a strong increasing trend with higher HPV load (lower HPV 16 $C_t$) (Table 2). In these analysis we adjusted for the effect of differences in amount of genomic DNA using the mean β-actin $C_t$ values. As shown in Table 2 (under Ct-HPV mean) the OR for the percentile including smears with the highest viral load (Ct<36.66) indicate an almost 70-fold higher risk relative to women testing negative for HPV. Similarly, for smears in the percentile with Ct values in the interval 36.66–38.99 the OR indicate a 19-fold higher risk, for Ct values in the interval 38.99–41.25 an 8-fold higher risk, for Ct values in the interval 41.25–44.8 a 4-fold higher risk and for Ct values in the interval 44.8–50 a 2-fold higher risk.

Statistically significant increasing ORs with higher HPV 16 load are also observed using only the smear with the minimum, or maximum, $C_t$ value from an individual woman. This may imply that over time individual women tend to have either low or high HPV titre.

Finally, the OR based on only the first HPV 16 positive smear from each woman, taken on average 7.8 years before diagnosis, is still significant for all the percentiles, except the first, and also show a strong increasing trend with higher viral load (Table 3). As shown in Table 3 women from which a single smear was collected, at a time before any cytological abnormalities are found, and with a Ct<35.9 have a 60-fold increased risk of developing cervical cancer relative to women testing HPV negative. Similarly, women with a Ct between 35.9–38.7 have a 19-fold increased risk, women with a Ct between 38.7–42.08 have a 23-fold increased risk, women with a Ct between 42.08–45.26 have a 7-fold increased risk, and finally, women with a Ct between 45.26–50 have a 1.8-fold increased risk of developing cervical cancer as compared to HPV negative women. Since only one smear has been included per women the relationship between high viral load (low HPV 16 $C_t$) and risk of cancer is not due to dependence among smears. Also, the results in comparing only the first positive smear from each woman cannot be due to asymmetric sampling of cases and controls, since there is no difference in the mean time between sampling and diagnosis for the cases and controls (data not shown).

TABLE 3

Results of conditional logistic regression analysis of the first smear of cases and controls among β-actin positive women.

| Categories* | HPV $C_t$ first smear OR (95% CI)† |
|---|---|
| HPV − | 1 |
| HPV +, $C_t$ [45.26; 50] | 1.88 (0.83–4.25) |
| HPV +, $C_t$ [42.08; 45.26] | 7.17 (2.68–19.14) |
| HFV +, $C_t$ [38.7; 42.08] | 22.78 (5.47–94.96) |
| HPV +, $C_t$ [35.9; 38.7] | 18.88 (5.49–64.86) |
| HPV +, $C_t$ <35.9 | 58.97 (7.52–462.24) |

* Categories are calculated on each 20 percentile of the distribution of the HPV 16 $C_t$ value for the first smear for each woman.
†Adjusted for β-actin.

These results demonstrate that increased HPV DNA viral load is a significant risk factor for cervical cancer. The cases and controls display a difference in viral load up to 8 years before the date of diagnosis of cancer in situ. Such a long-term difference in viral load could either be due to environmental or genetic risk factors. A number of environmental factors, such as sexual behaviour, smoking and variation in HPV subtype, earlier proposed to affect the risk of infection, could also, in principle, affect the viral load. The high OR may also reflect inherent differences between individuals in the response to HPV 16 infection.

Figure 3:
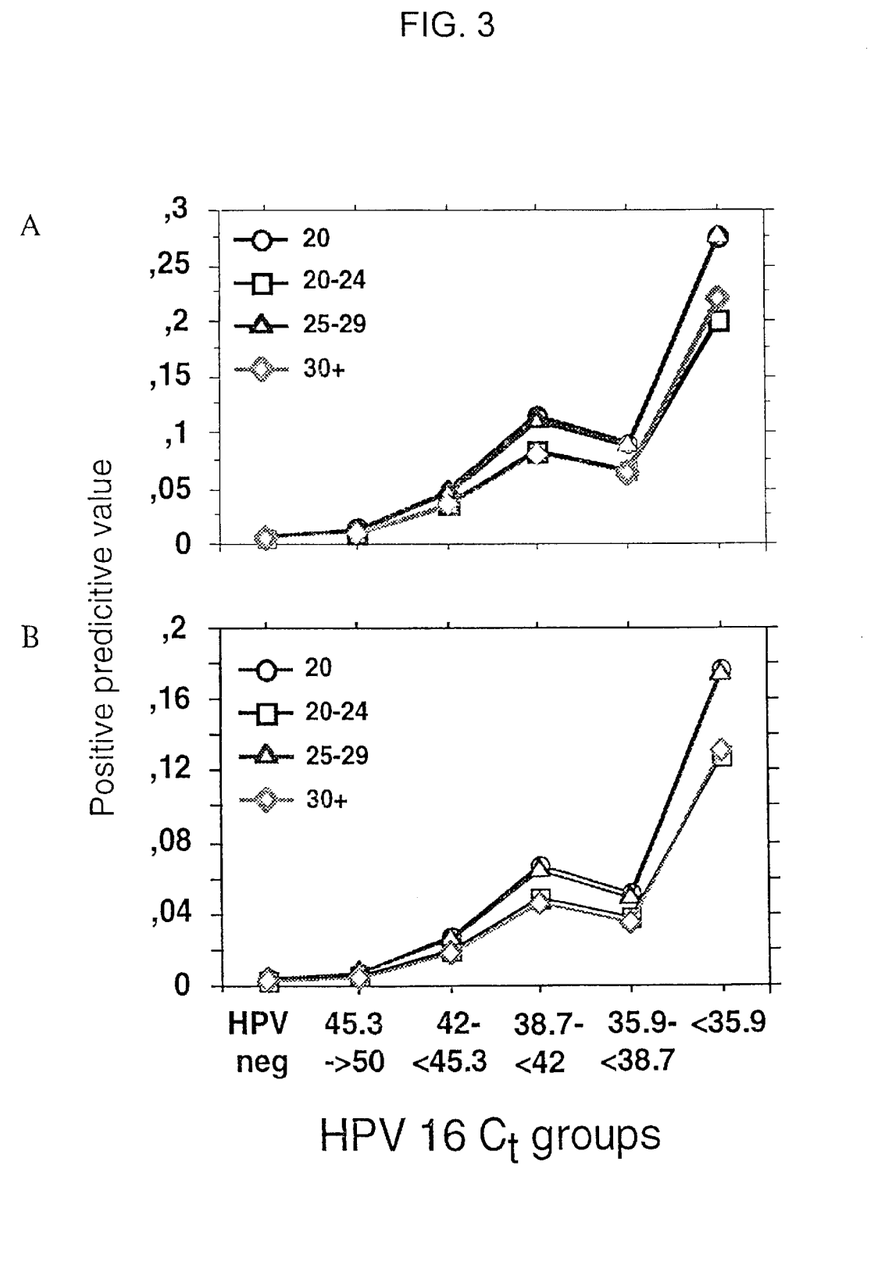
FIG. 3 shows positive predictive value (PPV) for women at different percentiles of the distribution of HPV 16 threshold cycle (Ct) values. The different categories of HPV 16 Ct values are from Table 2. Separate analyses were performed for smears with high amounts of nuclear DNA (β-actin Ct<34.78 (FIG. 4A)) and low amounts of nuclear DNA (β-actin Ct>34.87 (FIG. 4B)) since β-actin was found to be an effect modifier.

Given the very high OR for high HPV 16 viral loads, quantitation of oncogenic subtypes of HPV may have a clinical utility. Therefore, the positive predictive value (PPV), a measure of absolute risk, associated with different HPV 16 viral loads, was estimated from the case-control study, according to methods described. For this analysis no exclusion of smears taken within the last year before diagnosis was made. In the analysis using only the first smear from each woman, β-actin was found to be an effect modifier. Therefore, the smears were stratified into two groups with low and high β-actin $C_t$ values. The PPV increases consistently with viral load in all age groups and for both β-actin categories (FIG. 3). The probability of developing cervical cancer in situ for women with a HPV 16 negative first smear varies between 0.3–0.8%, while in the group with high nuclear DNA amount ($C_t$>34.78), the PPV for the percentile with the highest HPV viral load reaches over 27% in the youngest age group. Thus, a woman in her twenties from this populations and with a HPV 16 $C_t$ value in the highest percentile, has an absolute risk of 27% of developing cancer. This should be compared to the risk of a women testing negative in the same age-group of 0.8%, a likelihood ratio of 34.

In order to study the relationship between HPV 16 viral load and cytological screenings status, as determined by the PAP code, the median HPV 16 Ct value for different PAP code classes were calculated for the cases and controls (Table 4). PAP code 1 signifies cytologically normal smears. A clear correlation was seen between decreasing HPV 16 Ct values (increasing HPV titer) ad higher PAP code both among the cases and controls. Interestingly, the median among cytologically normal smears in the cases (PAP code 1)(HPV 16 Ct=38.7) was substantially lower than for the controls (HPV 16 Ct=44.3), attesting to the ability to use the HPV titer assay to identify women with a high risk of cancer development at such an early stage that present screening tools (such as PAP smears) are uninformative.

TABLE 4

HPV Ct values in relation to cytological diagnosis (PAP code).

| Pap code | Cases Median HPV16 Ct (25–75% percentiles) | Controls |
|---|---|---|
| Missing | 41.5 (39.2–44.2) | 44.3 (42.3–45.1) |
| 1 | 38.7 (35.6–41.9) | 44.4 (40.4–46.9) |
| 2 | 37.0 (34.4–40.1) | 40.4 (36.6–41.9) |
| 3 | 36.1 (33.8–39.6) | — |
| 4 | 35.2 (33.1–38.7) | — |
| 5 | 33.4 (32.1–35.8) | — |

Notes:
Pap 1: normal epithelial cells, Pap 2: inflammation, no or slight epithelial atypia, Pap 3: moderate epithelial atypia, Pap 4–5: strong epithelial atypia.

Thus, HPV DNA viral load estimates may significantly improve the ability to distinguish between infections that have a high or low risk of progressing into cervical cancer in situ. Further, as noted, these absolute risk estimates were obtained using the first β-actin positive smear, which in most cases had no sign of dysplasia and were collected almost 8 years before diagnosis. Consequently, estimates of the HPV DNA viral load are likely to be informative at such an early stage in the development of cervical cancer in situ that preventive treatment can be very successful. The addition of a quantitative test of HPV viral load in conjunction with routine gynaecological health controls, thus, appears to be a simple and cost-effective means of identifying women prone to develop cervical cancer and, as a consequence, also reducing the incidence of cervical cancer.

In applying such a test a sample is obtained as part of the routine gynaecological health control and examined for the relative viral load (the HPV DNA amount, normalized for amount of sample). The measured relative viral load is then used, based on established risk relationships between viral load and cancer of the type described above, to assess the risk category for the individual. Dependent on the outcome of the assay (high or low risk category) different outcomes are recommended (e.g. continued follow-up, treatment).

What is claimed is:

1. A method to predict the risk of progression to virus-associated cancer in a human subject, comprising the steps of:
   a) measuring the amount of a viral nucleic acid sequence or fragment thereof in a sample from the human subject;
   b) measuring the amount of said sample;
   c) relating the value from a) to the value from b) to obtain a value of relative viral load in said sample,
   d) using said value to estimate risk of progression to cervical cancer, with an increasing viral load indicating an increasing risk of progression to cervical cancer.

2. A method according to claim 1, wherein the amount of said sample is measured by measuring a human nucleic acid sequence or fragment thereof.

3. A method according to claim 1, wherein the viral nucleic acid sequence is from cervical cancer associated human papillomavirus (HPV)-types.

4. A method according to claim 1, wherein the viral nucleic acid sequence is from oncogenic genital HPV types.

5. A method according to claim 4, wherein the viral nucleic acid sequence derives from the E1 gene, the E6 gene, the E7 gene, the L1 gene, or fragment(s) thereof.

6. A method according to claim 1, wherein the amount of said sample is measured by measuring a human nucleic acid sequence derived from a genomic nuclear gene, or by methods for determining the amount of biological sample such as by counting cells, cell staining, cell fluorescence, total DNA amount, using a technical device for obtaining identical amounts of biological sample, or using volume, weight or other means of normalizing for sample amount.

7. A method according to claim 1, wherein the viral and human nucleic acid sequences are DNA or RNA sequences and measuring in step a) and b) is made by methods for quantitative DNA or RNA analysis.

8. A kit for predicting the risk of progression to human Papilloma virus (HPV)-associated cervical cancer by amplification of viral nucleic acid, comprising
   a) primers specific for a region of the conserved E1 gene of oncogenic HPV types; which are HPVE116L 5'-TACAGGTTCTAAAACGAAAGT-3' specific for HPV 16 and HPVE116R 5'-TTCCACTTCAGTATTGCCATA-3' specific for HPV 16; and/or 5'-HPVE118L TGCATGTTTTAAAACGAAAGT-3' specific for HPV 18, and HPVE118R 5'-TTCCACTTCAGAACAGCCATA-3' specific for HPV 18.

9. A kit according to claim 8, also comprising b) primers specific for genomic DNA in a sample from a human subject.

10. A kit according to claim 9, wherein the primers in a) consist of a 5' primer mix of two primers
HPVE116L 5'-TACAGGTTCTAAAACGAAAGT-3' specific for HPV 16 and
5'-HPVE118L TGCATGTTTTAAAACGAAAGT-3' specific for HPV 18, and
a 3' primer mix consisting of the following three primers:
HPVE116R 5'-TTCCACTTCAGTATTGCCATA-3' specific for HPV 16,
HPVE118R 5'-TTCCACTTCAGAACAGCCATA-3' specific for HPV 18; and
HPVE1RE 5'-TRYRKGMNYTAAAACGAAAGT-3' specific for HPV types 30–60, wherein R=A or G, Y=C or T, K=G or T, M=A or C, S=G or C, W=A or T, N=A, T, C or G, B=C, G, or T, D=A, G, or T, H=A, C, or T, V=A, C or G.

11. A kit according to claim 9, also comprising DNA intercalating dye.

12. A kit according to claim 9, also comprising
c) labelled HPV specific probes; and d) labelled probes specific for human genomic DNA.

13. A kit according to claim 12, wherein the HPV specific probe is selected from:
HPV 16 probe: 5'-ATAATCTCCTTTTTGCAGCTCTACTTTGTTTTT-3'
HPV 18 probe: 5'-CCGCCTTTTTGCCTTTTTCTGCCCACTAATT-3'
HPV 31 probe: 5'-TCTTCGTTTTGCTGTTTTACTGTTATTTTCTAT-3'
HPV 33 probe: 5'-TTTTCGTTTTCTGTATGTGCATTCTTTATTTTT-3'
HPV 35 probe: 5'-TCGTCGCTTTCGTGCTGTATTTTTATTTTCA-3'.

14. A method of predicting the risk of progression to virus-associated cervical cancer in a human subject, comprising the steps of:

determining a concentration of a viral load in a sample from a human subject; and assessing the risk of progression to cervical cancer based on the determined concentration, wherein, the human subject is free of cytological changes.

* * * * *

SEQUENCE LISTING

<160> NUMBER OF SEQ ID NOS: 11

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Probe

<400> SEQUENCE: 1
ataatctcct ttttgcagct ctactttgtt ttt         33

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Probe

<400> SEQUENCE: 2
ccgccttttt gccttttct gcccactaat t            31

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Probe

<400> SEQUENCE: 3
tcttcgtttt gctgttttac tgttattttc tat         33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Probe

<400> SEQUENCE: 4
ttttcgtttt ctgtatgtgc attctttatt ttt         33

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Probe

<400> SEQUENCE: 5
tcgtcgcttt cgtgctgtat ttttattttc a           31

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
tacaggttct aaaacgaaag t                      21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 7
tgcatgtttt aaaacgaaag t                      21

<210> SEQ ID NO 8
<211> LENGTH: 21
<212> TYPE: DNA

```
<213> ORGANISM: Artificial Sequence
<220> FEATURE:
<223> OTHER INFORMATION: Description of Artificial Sequence: Primer

<400> SEQUENCE: 8
ttccacttca gtattgccat a                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 9
ttccacttca gaacagccat a                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer
<220> FEATURE:
<221> NAME/KEY: modified_base
<222> LOCATION: (8)
<223> OTHER INFORMATION: A, T, C or G

<400> SEQUENCE: 10
tryrkgmnyt aaaacgaaag t                                              21

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Probe

<400> SEQUENCE: 11
ataatctcct ttttgcagct ctactttgtt ttt                                 33
```